United States Patent [19]

Futami et al.

[11] Patent Number: 5,698,610
[45] Date of Patent: Dec. 16, 1997

[54] LOW-DUST DENTAL ALGINATE IMPRESSION MATERIAL COMPOSITION

[75] Inventors: Shunichi Futami; Nobutaka Watanabe, both of Tokyo, Japan

[73] Assignee: GC Corporation, Tokyo, Japan

[21] Appl. No.: 779,236

[22] Filed: Jan. 3, 1997

[30] Foreign Application Priority Data

Jan. 24, 1996 [JP] Japan ................... 8-028691

[51] Int. Cl.[6] ................... A61K 6/10; A61C 9/00; C09K 3/22; C08L 5/04
[52] U.S. Cl. ................... 523/109; 106/35; 106/38.51; 106/205.1; 106/205.9; 433/214; 524/28; 524/456; 524/546
[58] Field of Search ................... 106/35, 38.51, 106/205.1, 205.2, 205.9; 433/214; 523/109; 524/28, 456, 546

[56] References Cited

U.S. PATENT DOCUMENTS

| | | | |
|---|---|---|---|
| 4,515,913 | 5/1985 | Pellico | 523/109 |
| 4,543,372 | 9/1985 | Watanabe et al. | 523/109 |
| 4,670,053 | 6/1987 | Kooke et al. | 433/214 |
| 4,695,322 | 9/1987 | Schwabe et al. | 106/35 |

*Primary Examiner*—Peter A. Szekely
*Attorney, Agent, or Firm*—Oblon, Spivak, McClelland, Maier & Neustadt, P.C.

[57] ABSTRACT

A low-dust dental alginate impression material composition is disclosed, comprising an alginate, a gelation reaction agent, a gelation regulator, and a filler as major components, which further comprises sepiolite and/or a tetrafluoroethylene resin having a true specific gravity of from 2.0 to 3.0. The low-dust dental alginate impression material composition of the present invention does not influence various capacities of the alginate impression material itself at all, is reduced in the generation of dust, and is superior in the storage stability.

3 Claims, No Drawings

LOW-DUST DENTAL ALGINATE IMPRESSION MATERIAL COMPOSITION

FIELD OF THE INVENTION

The present invention relates to a dental alginate impression material composition to be provided in a powder state. In particular, the present invention relates to a low-dust dental alginate impression material composition that reduces the flying of dust at the time of measuring or mixing of powder.

BACKGROUND OF THE INVENTION

A dental alginate impression material composition (hereinafter sometimes referred to as an "alginate impression material") is composed of an alginate, a gelation reaction agent, a gelation regulator, and a filler as major components and is mainly used for impression taking in the mouth. Since this alginate impression material is cheap, is easy for impression operations, and has a proper precision, it is most commonly used as a dental impression material. At the time of using it, a predetermined amount of the alginate impression material is mixed with water to form a paste, which is then load on an impression tray, is inserted in the mouth, and is kept upon pressure holding, and when the paste is gelled to form an elastic body, this elastic body is taken out from the mouth to effect the impression taking.

Since the alginate impression material is mixed with water to readily form a paste, from which is formed a homogeneous gel elastic body, it is provided in the state of a fine powder, and as a method for measuring a predetermined amount of the alginate impression material, in general, the measure by using an exclusive spoon with a fixed volume is commonly used. However, since the alginate impression material powder has such properties that during the storage in a vessel, it causes sedimentation, whereby the bulk density of the powder itself gradually changes, an operation in which before the measure by using a spoon, the bulk density of the sedimented powder is returned to the lowest state by shaking the vessel or other means is necessary. In this case, when a lid is opened after shaking the vessel, a phenomenon in which dust fly out as anemophilies occurs. Also, at the time of stirring operations by using a spatula during mixing a predetermined amount of the alginate impression material powder with water, dust tend to generate. Such a phenomenon of the generation of dust not only gives users unpleasant feelings but also possibly causes environmental pollution or injures the health, and hence, is pointed out to be a drawback of the alginate impression material.

In order to solve this drawback, the reduction of dust is being carried out by a method as proposed in Japanese Patent Laid-Open No. 57-501426, in which the powder particles of the alginate impression material is coated with a coating material capable of being wetted easily and rapidly by water, or by a method as proposed in Japanese Patent Laid-Open No. 60-105607, in which a hydrophobic hydrocarbon or silicone oil is contained in the alginate impression material powder.

However, since in any of these methods for reduction of dust, liquid substances are contained in the alginate impression material, the properties of the alginate impression material powder are influenced not a few. That is, the alginate impression material as disclosed in Japanese Patent Laid-Open No. 57-501426 has such a drawback that the hydrophilic coating material increases the water absorption properties of the alginate impression material so that the depolymerization of the alginate caused by the presence of water, or the mutual reaction between the alkaline component and the acidic component, is promoted, whereby the degradation of qualities is accelerated, and the storage stability is inferior; and the alginate impression material as disclosed in Japanese Patent Laid-Open No. 60-105607 has such a drawback that the hydrophobic substance reduces the mixing properties of the alginate impression material powder with water.

In addition, in these cases of the reduction of dust by liquid substances, since the alginate impression material powder is always in a wet state, the flow of the powder is so bad that a phenomenon in which the measure of a fixed amount of the powder by means of a spoon is difficult, or the like occurs. Also, there is a fear that the liquid component causes denaturation in the storage over a long period of time.

SUMMARY OF THE INVENTION

An object of the present invention is to solve the drawbacks of the conventional technologies as described above and provide an alginate impression material having superior low-dust properties and storage stability without causing any influences against various capacities of the alginate impression material powder.

In order to achieve the above-described object, the present inventors made extensive and intensive investigations. As a result, it has been found that if sepiolite and/or a tetrafluoroethylene resin exhibiting powder properties is contained in an alginate impression material powder component, a low-dust alginate impression material powder can be obtained without using a liquid component, leading to accomplishment of the present invention.

DETAILED DESCRIPTION OF THE INVENTION

That is, the sepiolite is a natural mineral fiber containing magnesium silicate as a major component and has such a state that the fibers are tangled with each other. If it is mixed in an alginate impression material powder at the time of production, the fine particles in the alginate impression material powder component are trapped in the tangled fibers or a part of the frayed portions of the fibers, whereby the generation of dust is reduced.

Also, the tetrafluoroethylene resin is a resin having such properties that upon application with a stress, it exhibits a cobweb-like fibrous state. If the tetrafluoroethylene resin is mixed in an alginate impression material powder at the time of production, it becomes in a cobweb-like state due to the stress applied at the time of mixing and traps the fine particles in the alginate impression material powder component, whereby the generation of dust is reduced.

In the light of the above, the present invention provides a low-dust dental alginate impression material composition based on a quite novel conception that a low-dust effect is obtained by using a powder component of sepiolite and/or a tetrafluoroethylene resin.

That is, the low-dust dental alginate impression material composition according to the present invention is a dental alginate impression composition composed of an alginate, a gelation reaction. agent, a gelation regulator, and a filler as major components, which is characterized by containing sepiolite and/or a tetrafluoroethylene resin having a true specific gravity of from 2.0 to 3.0. The sepiolite and/or the tetrafluoroethylene resin preferably has a mean particle size of from 1 to 40 µm and is contained in an amount of from 0.5 to 20% by weight.

As the dental alginate impression material component in the low-dust dental alginate impression material composition according to the present invention, any of powdery alginate impression materials that are usually used for the dental purpose can be used, and it is composed of an alginate, a gelation reaction agent, a gelation regulator, and a filler as major components.

As the alginate, at least one of water-soluble alginic acid salts such as sodium alginate, potassium alginate, ammonium alginate, and triethanolamine is used, and usually, it is contained in an amount of from about 10 to 20% by weight in the alginate impression material.

As the gelation reaction agent, sparingly soluble metal salts having a valence of 2 or more are used, and preferably, a dihydrate or hemihydrate of calcium sulfate is used. Usually, it is contained in an amount of from about 10 to 20% by weight in the alginate impression material.

As the gelation regulator, at least one of various phosphates, silicates and carbonates of sodium or potassium is used, and usually, it is contained in an amount of from about 1 to 5% by weight in the alginate impression material.

As the filler, at least one powder of diatomaceous earth, silicic acid anhydride, talc, calcium carbonate, and perlite is used, and usually, it is contained in an amount of from about 40 to 75% by weight in the alginate impression material.

In addition to these major components, if desired, metallic oxides, hydroxides or fluorides as gelation reinforcing agents, colorants, reodorants, and the like can be compounded. The components and compositions of the dental alginate impression material which is used in the present invention are not particularly limited.

The present invention is characterized by containing sepiolite and/or a tetrafluoroethylene resin having a true specific gravity of from 2.0 to 3.0 so as to trap the fine particles in the alginate impression material powder to thereby reduce the generation of dust.

The sepiolite is a natural mineral fiber containing naturally yielded magnesium silicate [$Mg_8Si_{12}O_{30}(OH)_4(OH_2)_4 \cdot 8H_2O$] as a major component and has such a state that the fibers are tangled with each other. If the sepiolite is contained together with the above-described respective powder components during the production of an alginate impression material, the fine particles in the alginate impression material powder component are trapped in the tangled fibers of sepiolite or partly frayed portions of the fibers at the time of mixing of the powder components, whereby the generation of dusts is reduced. Also, the sepiolite has a strong affinity with water so that it has an effect for acting as a thickening agent of the alginate impression material to improve the compression strength. Also, unexpectedly, it has become clear that the sepiolite has a good adaptation to gypsum so that it has an effect for smoothing the surface of a gypsum model prepared based on the impression taken by using an alginate impression material.

The tetrafluoroethylene resin is a linear polymer having a structure of —($CF_2$—$CF_2$)n— and is a finely particulate resin having tetrafluoroethylene polymerized in an aqueous solution. The molecular chain of this fine resin has a low intermolecular cohesive force, and therefore, this resin has such a property that upon application with a few compression or shear stress, it becomes a fine cobweb-like fiber. If the tetrafluoroethylene resin is contained together with the above-described powder components during the production of an alginate impression material, at the time of mixing of the powder components, the tetrafluoroethylene resin is applied with a stress and changes to a fine cobweb-like state, whereby the fine particles in the alginate impression material powder component are trapped to reduce the generation of dust. Also, the tetrafluoroethylene resin is hydrophobic so that it has an effect for improving the storage stability of the alginate impression material. Further, since the tetrafluoroethylene resin has a low surface friction coefficient and is hardly adhered, it has such effects that the flow of the alginate impression material powder is made smooth and that at the time of mixing with water, the water is gradually penetrated into the alginate impression material powder, to thereby enable to readily obtain a smooth paste.

The sepiolite and tetrafluoroethylene resin for reducing the generation of dusts in the alginate impression material powder can be used either alone or in admixture. Any of the sepiolite and tetrafluoroethylene resin which can be used in the present invention have a true specific gravity of from 2.0 to 3.0. In case that the true specific gravity is less than 2.0, they are too light and tend to fly themselves, whereby a satisfactory effect for reducing the generation of dusts can not be obtained. On the other hand, in case that the true specific gravity exceeds 3.0, they are too heavy and tend to sediment themselves in the powder, whereby the dispersibility of the powder is reduced, and hence, such is improper.

Also, any of the sepiolite and tetrafluoroethylene resin preferably have a mean particle size of from 1 to 40 μm. In case that the mean particle size is less than 1 μm, the effect for trapping the fine powder particles in the alginate impression material tends to be lowered, while in case that the mean particle size exceeds 40 μm, the fluidity of the impression material powder is lowered, and the scattering in the scoopfull amount by means of a spoon becomes large, whereby the measure of a fixed amount tends to be difficult. A suitable content of the sepiolite and/or tetrafluoroethylene resin is in the range of from 0.5 to 20% by weight, and preferably from 2 to 15% by weight. In case that the content is less than 0.5% by weight, the effect for reducing the generation of dust tends to be lowered, while in case that the content exceeds 20% by weight, no further improvements in the effect for reducing the generation of dusts are expected, but the properties of the sepiolite or tetrafluoroethylene resin become rather strong, whereby the alginate impression material powder tends to become in a cotton-like state.

As described above, in the present invention, the powdery sepiolite and/or tetrafluoroethylene resin exhibiting a fibrous structure is contained in the powdery alginate impression material composition to obtain a low-dust dental alginate impression material composition. As a matter of course, the present invention can be combined with the conventional method for reducing the generation of dust in which liquid components such as hydrophilic substances and hydrophobic substances are used.

The low-dust dental alginate impression material composition according to the present invention will be hereunder described in more detail with reference to the following Examples, but it is to be not construed that the present invention is limited to the descriptions of the Examples.

EXAMPLE 1

| | |
|---|---|
| Sodium alginate | 15 (% by weight) |
| Calcium sulfate dihydrate | 15 |
| Trisodium phosphate | 2 |
| Diatomaceous earth | 57 |
| Potassium titanium fluoride | 1 |
| Aluminum oxide | 2 |

| Sepiolite (true specific gravity: 2.6, mean particle size: 15 μm) | 8 |

The above-described respective components were thoroughly mixed in a blender to obtain a low-dust dental alginate impression material composition.

EXAMPLE 2

| Sodium alginate | 13 (% by weight) |
| --- | --- |
| Calcium sulfate dihydrate | 15 |
| Trisodium phosphate | 2 |
| Diatomaceous earth | 60 |
| Talc | 3 |
| Potassium titanium fluoride | 1 |
| Aluminum oxide | 2 |
| Tetrafluoroethylene resin (true specific gravity: 2.2, mean particle size: 5 μm) | 4 |

The above-described respective components were thoroughly mixed in a blender to obtain a low-dust dental alginate impression material composition.

EXAMPLE 3

| Potassium alginate | 16 (% by weight) |
| --- | --- |
| Calcium sulfate dihydrate | 17 |
| Trisodium phosphate | 2 |
| Silicic anhydride | 7 |
| Diatomaceous earth | 35 |
| Perlite | 10 |
| Potassium silicofluoride | 1 |
| Zinc oxide | 2 |
| Tetrafluoroethylene resin (true specific gravity: 2.1, mean particle size: 25 μm) | 10 |

The above-described respective components were thoroughly mixed in a blender to obtain a low-dust dental alginate impression material composition.

EXAMPLE 4

| Potassium alginate | 12 (% by weight) |
| --- | --- |
| Calcium sulfate dihydrate | 14 |
| Trisodium phosphate | 2 |
| Silicic anhydride | 5 |
| Diatomaceous earth | 44 |
| Perlite | 5 |
| Potassium silicofluoride | 1 |
| Zinc oxide | 2 |
| Sepiolite (true specific gravity: 2.5, mean particle size: 33 μm) | 15 |

The above-described respective components were thoroughly mixed in a blender to obtain a low-dust dental alginate impression material composition.

EXAMPLE 5

| Potassium alginate | 18 (% by weight) |
| --- | --- |
| Calcium sulfate dihydrate | 19 |
| Trisodium phosphate | 2 |
| Silicic anhydride | 8 |
| Diatomaceous earth | 33 |
| Perlite | 7 |
| Potassium silicofluoride | 1 |
| Zinc oxide | 2 |
| Sepiolite (true specific gravity: 2.5, mean particle size: 20 μm) | 7 |
| Tetrafluoroethyolene resin (true specific gravity: 2.2, mean particle size: 20 μm) | 3 |

The above-described respective components were thoroughly mixed in a binder to obtain a low-dust dental alginate impression material composition.

COMPARATIVE EXAMPLE 1

| Sodium alginate | 15 (% by weight) |
| --- | --- |
| Calcium sulfate dihyrate | 15 |
| Trisodium phosphate | 2 |
| Diatomaceous earth | 60 |
| Talc | 5 |
| Potassium titanium fluoride | 1 |
| Aluminum oxide | 2 |

The above-described respective components were thoroughly mixed in a blender to obtain a dental alginate impression material composition.

COMPARATIVE EXAMPLE 2

| Sodium alginate | 15 (% by weight) |
| --- | --- |
| Calcium sulfate dihydrate | 15 |
| Trisodium phosphate | 2 |
| Diatomaceous earth | 56 |
| Talc | 5 |
| Potassium titanium fluoride | 1 |
| Aluminum oxide | 2 |
| Polypropylene glycol | 4 |

The diatomaceous earth and talc were previously coated with the polyethylene glycol and then thoroughly mixed together with the remaining respective components in a blender to obtain a low-dust dental alginate impression material composition.

COMPARATIVE EXAMPLE 3

| Potassium alginate | 16 (% by weight) |
| --- | --- |
| Calcium sulfate dihydrate | 17 |
| Trisodium phosphate | 2 |
| Silicic anhydride | 7 |
| Diatomaceous earth | 40 |
| Perlite | 10 |
| Potassium silicofluoride | 1 |
| Zinc oxide | 2 |
| Liquid paraffin | 4 |
| Polyvinylpyrrolidone | 1 |

First of all, the above-described respective components other than the liquid paraffin were mixed in a blender, and the mixing was then continued in the blender while adding dropwise the liquid paraffin thereto, to obtain a low-dust dental alginate impression material composition.

With respect to the alginate impression material compositions of the respective Examples and Comparative Examples, not only the weight concentrations of dust were compared, but also by mixing 16 parts by weight of the powder with 40 parts by weight of water, the gelation time and compressive strength according to the Japanese Industrial Standard, JIS T 6505 were measured before and after the forced storage. Also, the surface roughness of gypsum set after placing a dental model stone slurry on the impression surface of a gel elastic body of this alginate impression material composition was measured according to JIS B 0601 and compared. The results obtained are summarized in Table 1. The forced storage was carried out in such a manner that each powder was sealed by an aluminum pack and stored at a temperature of 60° C. and at a humidity of 100% for 7 days.

impression material of each of the Examples is smooth as compared with that in each of the Comparative Examples. In particular, it could be confirmed that the surface roughness of the gypsum even after the forced storage does not change at all and keeps the superior smoothness. Also, it was confirmed that the low-dust dental alginate impression material composition according to the present invention exhibits a high compression strength as compared with that in each of the Comparative Examples, enables to achieve impression taking with less deformation, and even after the forced storage, has a stable gelation time and compressive strength, and is superior in the storage stability.

TABLE 1

| | Weight concentration of dust (mg/m³) | Before the forced storage | | | After the forced storage | | |
|---|---|---|---|---|---|---|---|
| | | Gelation time | Compressive strength (MPa) | Surface roughness of gypsum (μm) | Gelation time | Compressive strength (MPa) | Surface roughness of gypsum (μm) |
| Example 1 | 8.5 | 2'10" | 1.00 | 8.2 | 2'20" | 0.96 | 8.2 |
| Example 2 | 9.8 | 2'10" | 0.93 | 8.5 | 2'10" | 0.88 | 8.6 |
| Example 3 | 7.0 | 2'30" | 1.05 | 9.0 | 2'30" | 0.99 | 9.1 |
| Example 4 | 6.7 | 2'30" | 1.20 | 6.8 | 2'20" | 1.13 | 6.8 |
| Example 5 | 8.0 | 2'30" | 1.02 | 7.0 | 2'10" | 0.98 | 7.1 |
| Comparative Example 1 | 48.5 | 2'10" | 0.83 | 13.0 | 2'40" | 0.66 | 15.2 |
| Comparative Example 2 | 6.0 | 2'10" | 0.76 | 15.0 | 3'10" | 0.35 | 18.3 |
| Comparative Example 3 | 4.5 | 2'30" | 0.80 | 11.5 | 2'40" | 0.70 | 13.6 |

[Measurement of Weight Concentration of Dust]

150 g of a powder sample was taken into a plastic vessel (155 mm W×155 mm D×155 mm H), after closing a lid, the vessel was shaken up and down reciprocally per second, and the shaking was carried out five times. Immediately thereafter, the lid was opened, and dusts released from the vessel were measured in terms of weight concentration for 3 minutes by means of a digital dust measuring apparatus (Model P-5, manufactured by Shibata Chemical Co., Ltd.).

[Measurement of Surface Roughness of Gypsum]

An alginate impression material paste prepared by mixing 16 parts by weight of the powder with 40 parts by weight of water was placed on a plastic plate (100 mm W×100 mm D×4 mm T), brought into contact under pressure with another plastic plate having the same dimension, and soaked in warm water (35° C.) for 2 minutes to thereby gel the impression material. The upper-sided plastic plate was left, a plaster slurry mixed with a dental model stone (a trade name: New Plastone, manufactured by GC Corporation) according to the indications of the manufacturer was placed on the impression surface, and after allowing to stand for 30 minutes to thereby set the gypsum, the gypsum was taken out from the impression material surface. After allowing to stand at room temperature over a whole day and night, a mean 10-point roughness was measured by using a surface roughness measuring apparatus (Surfcorder Model SE-40D, manufactured by Kosaka Kenkyusho K.K.).

As is clear from Table 1, it could be confirmed that the low-dust dental alginate impression material composition in each of the Examples according to the present invention exhibits substantially the same amount of dust as in the conventional low-dust dental alginate impression material using a liquid component in each of Comparative Examples 2 and 3 and is less in the generation of dust at the time of use and that the surface roughness of the gypsum prepared by pouring into the impression surface taken by using the That is, it can be said that the low-dust dental alginate impression material composition according to the present invention is a low-dust dental alginate impression material composition which is freed from any reduction in the gelation time, the compressive strength, and the surface roughness of gypsum after the forced storage and can keep the extremely stable capacities even after the storage over a long period of time.

As described above, the low-dust dental impression material composition according to the present invention contains a powder component of sepiolite and/or a tetrafluoroethylene resin that traps fine particles in the alginate impression material powder to thereby reduce the generation of dust, and hence, does not adversely affect the capacities of the alginate impression material itself at all, is able to provide an ideal low-dust dental alginate impression material composition having extremely superior storage stability, and is greatly valuable for contribution to the dental field.

While the present invention has been described in detail and with reference to specific embodiments thereof, it will be apparent to one skilled in the art that various changes and modifications can be made therein without departing from the spirit and scope thereof.

What is claimed is:

1. A low-dust dental alginate impression material composition comprising an alginate, a gelation reaction agent, a gelation regulator, and a filler as major components, which further comprises sepiolite and/or a tetrafluoroethylene resin having a true specific gravity of from 2.0 to 3.0.

2. A low-dust dental alginate impression material composition as claimed in claim 1, wherein said sepiolite and/or said tetrafluoroethylene resin has a mean particle size of from 1 to 40 μm.

3. A low-dust dental alginate impression material composition as claimed in claims 1 or 2, wherein said sepiolite and/or said tetrafluoroethylene resin is contained in an amount of from 0.5 to 20% by weight.

* * * * *